United States Patent
Paydar et al.

(10) Patent No.: US 9,976,801 B2
(45) Date of Patent: *May 22, 2018

(54) COMPUTER CONTROLLED AND MONITORED MEDICAL STORAGE SYSTEM

(71) Applicant: Omnicell, Inc., Mountain View, CA (US)

(72) Inventors: Akbar Paydar, Mountain View, CA (US); Stanley Kim, Mountain View, CA (US); Andrew Chai, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/381,384

(22) Filed: Dec. 16, 2016

(65) Prior Publication Data

US 2017/0122656 A1    May 4, 2017

Related U.S. Application Data

(63) Continuation of application No. 14/312,271, filed on Jun. 23, 2014, now Pat. No. 9,523,534, which is a (Continued)

(51) Int. Cl.
  *G08B 17/00*    (2006.01)
  *F25D 29/00*    (2006.01)
  (Continued)

(52) U.S. Cl.
  CPC .......... *F25D 29/008* (2013.01); *F25D 29/00* (2013.01); *G01K 3/005* (2013.01); *G01K 3/04* (2013.01);
  (Continued)

(58) Field of Classification Search
  CPC .... F25D 29/008; F25D 29/00; G06F 19/3462; G07F 9/105; G07F 17/0092;
  (Continued)

(56) References Cited

U.S. PATENT DOCUMENTS

| 4,368,867 A | 1/1983 | Pendleton et al. |
| 4,372,515 A | 2/1983 | Noonan |

(Continued)

FOREIGN PATENT DOCUMENTS

| CH | 688607 A5 | 12/1997 |
| CN | 101785021 A | 7/2010 |

(Continued)

OTHER PUBLICATIONS

Advertisement for Ergotron Mobile Work Centers Integrated Design and Manufacturing Feb. 1997 1 page.

(Continued)

*Primary Examiner* — Anh V La
(74) *Attorney, Agent, or Firm* — Kilpatrick Townsend & Stockton LLP

(57) ABSTRACT

A system is disclosed for monitoring and controlling a refrigerated medical storage unit. The system may include a control station. The control station may receive temperature information from the refrigerated medical storage unit and may cause at least a portion of the temperature information to be stored. The control station may determine whether the temperature is outside a predefined range and may causes an alarm to be generated when the temperature is outside the predefined range. The control station may receive user authentication information from a user, and upon verification of the user authentication information, send unlock instructions to the refrigerated medical storage unit.

17 Claims, 3 Drawing Sheets

Related U.S. Application Data continuation of application No. 13/312,374, filed on Dec. 6, 2011, now Pat. No. 8,773,270.

(60) Provisional application No. 61/420,262, filed on Dec. 6, 2010.

(51) Int. Cl.

| | |
|---|---|
| *G01K 3/00* | (2006.01) |
| *G01K 3/04* | (2006.01) |
| *G07F 9/10* | (2006.01) |
| *G07F 11/00* | (2006.01) |
| *G07F 17/00* | (2006.01) |
| *G06F 19/00* | (2018.01) |
| *A61B 50/00* | (2016.01) |
| *A61B 50/10* | (2016.01) |
| *A61B 50/30* | (2016.01) |

(52) U.S. Cl.
CPC .......... *G06F 19/3462* (2013.01); *G07F 9/105* (2013.01); *G07F 11/002* (2013.01); *G07F 17/0092* (2013.01); *A61B 50/10* (2016.02); *A61B 50/30* (2016.02); *A61B 2050/0014* (2016.02); *Y10T 307/352* (2015.04)

(58) Field of Classification Search
CPC ........ G07F 11/002; G01K 3/04; G01K 3/005; Y10T 307/352; A61B 50/10; A61B 50/30; A61B 2050/0014
USPC .......................... 340/585, 5.73, 542; 62/129
See application file for complete search history.

(56) References Cited

U.S. PATENT DOCUMENTS

| | | |
|---|---|---|
| 4,471,931 A | 9/1984 | Covey et al. |
| D279,007 S | 5/1985 | Empson et al. |
| 4,556,189 A | 12/1985 | Kirpluk et al. |
| 4,561,620 A | 12/1985 | Goetz et al. |
| 4,575,033 A | 3/1986 | Henneberg et al. |
| 4,589,621 A | 5/1986 | Hunt et al. |
| 4,616,218 A | 10/1986 | Bailey et al. |
| 4,640,199 A | 2/1987 | Zigman |
| 4,645,153 A | 2/1987 | Granzow et al. |
| D289,873 S | 5/1987 | Gemmell et al. |
| D293,382 S | 12/1987 | Ichikawa |
| 4,717,112 A | 1/1988 | Pirkle |
| 4,726,633 A | 2/1988 | Noble et al. |
| 4,729,533 A | 3/1988 | Hillary et al. |
| D295,415 S | 4/1988 | Thies et al. |
| 4,769,634 A | 9/1988 | Killian, Jr. et al. |
| 4,834,329 A | 5/1989 | Delapp |
| 4,836,478 A | 6/1989 | Sweere |
| 4,836,486 A | 6/1989 | Vossoughi et al. |
| 4,852,500 A | 8/1989 | Ryburg et al. |
| 4,918,841 A | 4/1990 | Turner et al. |
| 4,919,387 A | 4/1990 | Sampson |
| D310,358 S | 9/1990 | Nuttall et al. |
| 4,967,928 A | 11/1990 | Carter |
| D312,630 S | 12/1990 | Esslinger |
| 4,989,291 A | 2/1991 | Parent |
| D317,912 S | 7/1991 | Takai |
| D319,405 S | 8/1991 | Brawne |
| D319,435 S | 8/1991 | Brown |
| 5,039,928 A | 8/1991 | Nishi et al. |
| 5,041,770 A | 8/1991 | Seiler et al. |
| D326,847 S | 6/1992 | Savio |
| 5,174,223 A | 12/1992 | Nagy et al. |
| 5,217,064 A | 6/1993 | Kellow et al. |
| D337,104 S | 7/1993 | Orchard |
| D339,796 S | 9/1993 | Goodner et al. |
| 5,260,885 A | 11/1993 | Ma |
| 5,277,392 A | 1/1994 | Rossman et al. |
| 5,287,815 A | 2/1994 | Gross |
| D344,933 S | 3/1994 | Wiseman et al. |
| 5,321,579 A | 6/1994 | Brown et al. |
| D348,449 S | 7/1994 | Rodd et al. |
| D349,489 S | 8/1994 | Wang |
| 5,362,025 A | 11/1994 | Trom et al. |
| D354,052 S | 1/1995 | Imai |
| D354,952 S | 1/1995 | Rodd |
| D357,468 S | 4/1995 | Rodd |
| 5,437,235 A | 8/1995 | Randolph |
| 5,442,512 A | 8/1995 | Bradbury |
| 5,473,997 A | 12/1995 | Solomon et al. |
| 5,522,323 A | 6/1996 | Richard |
| 5,536,084 A | 7/1996 | Curtis et al. |
| D377,720 S | 2/1997 | Miller et al. |
| 5,630,566 A | 5/1997 | Case |
| 5,687,717 A | 11/1997 | Halpern et al. |
| 5,694,199 A | 12/1997 | Rodriguez |
| D393,382 S | 4/1998 | Rutter et al. |
| 5,738,316 A | 4/1998 | Sweere et al. |
| 5,772,637 A | 6/1998 | Heinzmann et al. |
| 5,775,234 A | 7/1998 | Solomon et al. |
| 5,806,943 A | 9/1998 | Dell et al. |
| 5,822,185 A | 10/1998 | Cavello |
| 5,842,672 A | 12/1998 | Sweere et al. |
| 5,868,079 A | 2/1999 | Charny |
| 5,897,179 A | 4/1999 | Wade |
| 5,918,841 A | 7/1999 | Sweere et al. |
| 5,960,901 A | 10/1999 | Hanagan |
| 5,971,341 A | 10/1999 | Pfister |
| 6,029,580 A | 2/2000 | Alfonso et al. |
| 6,061,104 A | 5/2000 | Evanicky et al. |
| 6,085,972 A | 7/2000 | Wright |
| 6,098,936 A | 8/2000 | Birrell |
| 6,170,929 B1 | 1/2001 | Wilson et al. |
| 6,175,779 B1 | 1/2001 | Barrett |
| 6,199,952 B1 | 3/2001 | Davis |
| 6,269,753 B1 | 8/2001 | Roddan |
| 6,298,794 B1 | 10/2001 | Brown et al. |
| 6,339,732 B1 | 1/2002 | Phoon et al. |
| 6,389,992 B1 | 5/2002 | Miller |
| 6,394,402 B2 | 5/2002 | Coonan et al. |
| 6,435,109 B1 | 8/2002 | Dell et al. |
| 6,493,220 B1 | 12/2002 | Clark et al. |
| 6,604,019 B2 | 8/2003 | Ahlin et al. |
| 6,721,178 B1 | 4/2004 | Clark et al. |
| 6,775,591 B1 | 8/2004 | Shoenfeld |
| 6,816,145 B1 | 11/2004 | Evanicky |
| 6,996,455 B2 | 2/2006 | Eggenberger et al. |
| 7,009,840 B2 | 3/2006 | Clark et al. |
| 7,026,929 B1 * | 4/2006 | Wallace ............. G08B 25/003 340/539.13 |
| 7,154,397 B2 | 12/2006 | Zerhusen et al. |
| 7,594,668 B2 | 9/2009 | Arceta et al. |
| 7,630,791 B2 | 12/2009 | Nguyen et al. |
| 7,747,347 B2 | 6/2010 | Park, IV |
| 8,180,485 B2 | 5/2012 | Reckelhoff |
| 8,196,939 B2 | 6/2012 | Bustle et al. |
| 8,773,270 B2 | 7/2014 | Paydar et al. |
| 9,523,534 B2 | 12/2016 | Paydar et al. |
| 2002/0000092 A1 | 1/2002 | Sharood et al. |
| 2003/0159076 A1 | 8/2003 | Delisle et al. |
| 2005/0140510 A1 | 6/2005 | Elwood et al. |
| 2005/0279122 A1 | 12/2005 | Cohen et al. |
| 2006/0005876 A1 | 1/2006 | Gaudiana et al. |
| 2006/0125356 A1 | 6/2006 | Meek, Jr. et al. |
| 2007/0228680 A1 | 10/2007 | Reppert et al. |
| 2009/0132090 A1 | 5/2009 | Kaczmarz et al. |
| 2009/0159608 A1 | 6/2009 | Shoenfeld |
| 2009/0231132 A1 | 9/2009 | Shoenfeld |
| 2009/0312656 A1 | 12/2009 | Lau et al. |
| 2010/0004780 A1 | 1/2010 | Rickelhoff |
| 2010/0042437 A1 | 2/2010 | Levy et al. |
| 2010/0106291 A1 | 4/2010 | Campbell et al. |
| 2010/0218021 A1 | 8/2010 | Ma et al. |
| 2010/0222649 A1 | 9/2010 | Schoenberg |
| 2010/0241446 A1 | 9/2010 | Eckert et al. |
| 2010/0275625 A1 | 11/2010 | Lowenstein |

(56) References Cited

U.S. PATENT DOCUMENTS

| | | |
|---|---|---|
| 2010/0300130 A1 | 12/2010 | Shoenfeld et al. |
| 2012/0203377 A1 | 8/2012 | Paydar et al. |
| 2012/0245731 A1 | 9/2012 | Reckelhoff |

FOREIGN PATENT DOCUMENTS

| | | |
|---|---|---|
| DE | 8114991 U | 10/1981 |
| DE | 295 06 433 U1 | 8/1995 |
| DE | 195 36 664 A1 | 4/1997 |
| DE | 196 42 425 A1 | 4/1998 |
| DE | 196 50 100 A1 | 6/1998 |
| EM | 0 321 137 A2 | 6/1989 |
| EP | 0 145 410 A2 | 6/1985 |
| EP | 0 796 575 A1 | 9/1997 |
| FI | 974408 A | 6/1999 |
| JP | 5161510 A | 6/1993 |
| JP | 9262137 A | 10/1997 |
| JP | 10-011172 | 1/1998 |
| JP | 10-057157 A | 3/1998 |
| JP | 10-146224 A | 6/1998 |
| JP | 11-127976 A | 5/1999 |
| JP | 2001-182394 A | 7/2001 |
| JP | 2001-343184 A | 12/2001 |
| JP | 2006-162106 A | 6/2006 |
| WO | 97/46824 A1 | 12/1997 |
| WO | 2012/078611 A1 | 6/2012 |
| WO | 2012/078676 A1 | 6/2012 |

OTHER PUBLICATIONS

Author Unknown "24" Wide AnthroCart" Anthro Technology Furniture Date Unknown [retrieved on Mar. 19, 2007] 4 pages. Retrieved from: http://web.archive.org/web/19970521181347/www.anthro.com/hprods_a/p_3.html.
Author Unknown "All the Right Moves . . . " Flat Panel Monitor Mounting Solutions Ergotron Inc. 1997 4 pages.
Author Unknown "CMS Business" Fieldlink Ergotron Nov. 1997 3 pages.
Author Unknown "Computer/Storage Cart" Milcare. Inc. 1997 2 pages.
Author Unknown "Ergotron ErgoCart" Product Bulletin Ergotron Inc. Dec. 1997 2 pages.
Author Unknown "Ergotron ErgoLift" Product Bulletin Ergotron Inc. Apr. 1999 3 pages.
Author Unknown "Evaluation Program: Mobile WorkCenter Solutions" Ergotron Inc. 1997 5 pages.
Author Unknown "Flat Panel Monitor Keyboard & Laptop" ARMS Product Guide Ergotron Inc. 1997 8 pages.
Author Unknown "Ira Goldklang's TRS-80 Revived Site: Model 200 Page" Aug. 5, 2007 [retrieved on Mar. 24, 2008] 3 pages. Retrieved from: http://www.trs-80.com/trs80-models-model200.htm.
Author Unknown "Korean Makers of TFT-LCD Likely to Have Brisk Year" AsiaPulse News Jan. 11, 1999 1 page.
Author Unknown "MediComp 2001 Options and Accessories" Jaco inc. 1997 1 page.
Author Unknown "MLT 2001: Variable Height Laptop/Peripheral Cart" Jaco Inc. 1997 3 pages.
Author Unknown "Mobile WorkCenter System"Ergotron Inc. 1997 5 pages.
Author Unknown "Mobile WorkCenters: Featuring Ergotron's Patented Monitor Suspension System" Ergotron Inc. 1994 4 pages.
Author Unknown "PCT-SC: Ergonomically designed Trans-Mobile self-contained clinical computing workstation system" Tremont Medical 1997 2 pages.
Author Unknown "Point-of-Care Carts as part of a Clinical Information System" MMP MedCart date unknown 8 pages.
Author Unknown "Point-of-Care: Cart Systems" MMP MedCart 1997 2 pages. Retrieved from: http://web.archive.org/web/19970301233615/www.medcart.com/pointof.html.
Author Unknown "Technology Furniture" Anthro Date Unknown 40 pages.
Author Unknown "Technology Furniture: New Product Update Fall 1996" Anthro 1996 12 pages.
Author Unknown "The Ergotron ErgoCart: A mobile and height adjustable solution for an entire computer system" Product Sheet Ergotron Inc. May 1999 2 pages.
Author Unknown "The Ergotron ErgoCart: A Mobile Solution for an entire computer system" Product Sheet Ergotron Inc. Apr. 1998 2 pages.
Author Unknown "The Nursing Station on Wheels" Infoport Sculptor Development Technologies Inc. Date Unknown [retrieved on Mar. 24, 2008] 2 pages. Retrieved from: http://www.sculptorsoftware.com/infoport.asp.
Author Unknown "Welcome to Ergotron" Ergotron Inc. 1996 [retrieved on Sep. 17, 2008] 1 page. Retrieved from: http://web.archive.org/web/19961104052222/http://www.ergotron.com/.
Bassak G. "Sharp picture Fuzzy Forecasting" Business & Company Resource Center Electronic Buyers' News Jan. 31, 2000 3 pages.
International Search Report and Written Opinion of PCT/US07/76336 dated Aug. 13, 2008 6 pages.
International Search Report and Written Opinion of PCT/US07/03765 dated Jun. 3, 2008 4 pages.
International Search Report and Written Opinion of PCT/US11/63597 dated Apr. 13, 2012 15 pages.
International Search Report and Written Opinion of PCT/US11/63505 dated Apr. 26, 2012 9 pages.
Japanese Patent Application No. 2013-543263 "Office Action" dated Oct. 10, 2017, 2 pages. (1 page for original office action 1 page for translation).

* cited by examiner

COMPUTER CONTROLLED AND MONITORED MEDICAL STORAGE SYSTEM

CROSS-REFERENCES TO RELATED APPLICATIONS

This application is a continuation of U.S. patent application Ser. No. 14/312,271, filed Jun. 24, 2014, entitled "COMPUTER CONTROLLED AND MONITORED MEDICAL STORAGE SYSTEM," which is a continuation of U.S. patent application Ser. No. 13/312,374, filed Dec. 6, 2011, issued as U.S. Pat. No. 8,773,374, and entitled "COMPUTER CONTROLLED AND MONITORED MEDICAL STORAGE SYSTEM," which claims the benefit of and priority to U.S. Provisional Patent Application No. 61/420,262, filed Dec. 6, 2010, entitled "MEDICATION DISPENSING CART." The entire disclosures of the above applications are hereby incorporated by reference, for all purposes, as if fully set forth herein.

BACKGROUND OF THE INVENTION

Temperature sensitive medications and supplies are common in today's healthcare environment. To maintain stability and potency, medications and other supplies may require proper storage based on guidelines set forth by the manufacturers of the medications and supplies, as well as the United States Pharmacopeia, the official public standards-setting authority in this field. For example, some injections and medications such as insulin, Lorazepam, and Epogen must be stored at a temperature of approximately 36° to 46° F. (2° to 8° C.) to maintain their viability. Additionally, many of these temperature sensitive medicines are controlled substances and necessitate stringent access and inventory controls.

Embodiments of the present invention provide solutions to these and other issues surrounding the storage of medication and other medical supplies.

BRIEF SUMMARY OF THE INVENTION

In one embodiment, a system for monitoring and controlling a refrigerated medical storage unit is provided. The system may include a control station. The control station may receive temperature information from the refrigerated medical storage unit and may cause at least a portion of the temperature information to be stored. The control station may determine whether the temperature is outside a predefined range and may causes an alarm to be generated when the temperature is outside the predefined range. The control station may receive user authentication information from a user, and upon verification of the user authentication information, send unlock instructions to the refrigerated medical storage unit.

In another embodiment, a method for monitoring and controlling an environmentally controlled medical storage unit is provided. The method may include receiving temperature information from the environmentally controlled medical storage unit. The method may also include causing at least a portion of the temperature information to be stored. The method may further include determining whether the temperature is outside a predefined range. The method may moreover include causing an alarm to be generated when the temperature is outside the predefined range. The method may furthermore include receiving user authentication information from a user. The method may additionally include verifying the user authentication information. The method may also include, in response to successfully verifying the user authentication information, causing the environmentally controlled medical storage unit to be unlocked.

In another embodiment, a system for monitoring and controlling a medical storage unit is provided. The control station may be remote from the medical storage unit. The control station may receive user authentication information from a user and, upon verification of the user authentication information, sends unlock instructions to the medical storage unit.

BRIEF DESCRIPTION OF THE DRAWINGS

The present invention is described in conjunction with the appended figures.

DETAILED DESCRIPTION OF THE INVENTION

Figure 1:
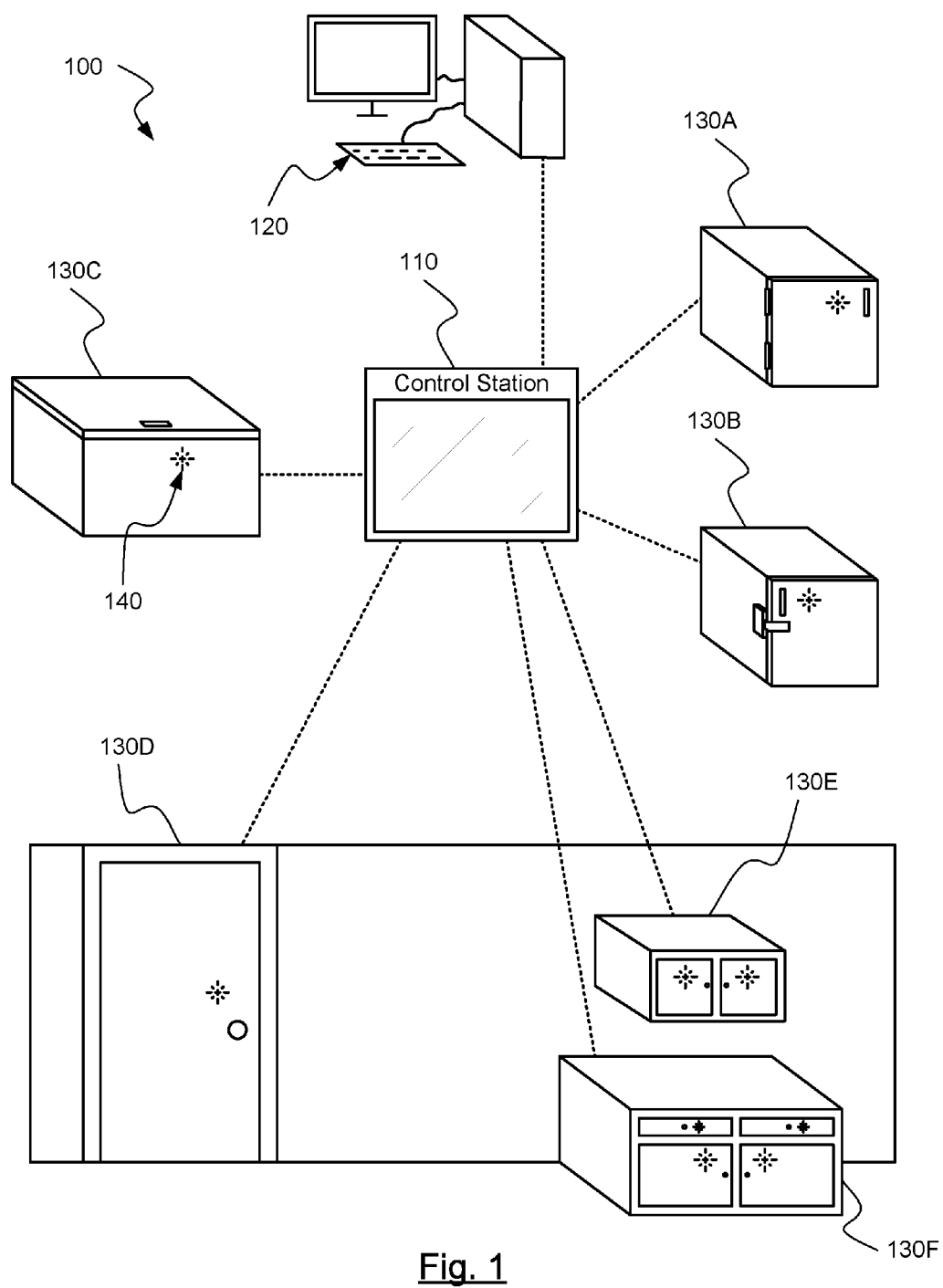
FIG. 1 is a structure diagram of a system of the invention for controlling and monitoring access and/or environmental parameters of medical storage units.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims. Merely by way of example, any embodiment described herein may or may not have any of the features discussed therewith, and may or may not have any feature discussed with respect to other embodiments.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In one embodiment of the invention, a system for monitoring and controlling both an environmentally controlled medical storage unit and a non-environmentally controlled medical storage unit is provided. Examples of environmentally controlled medical storage units include medical refrigerators and/or freezers (referred to as refrigerators and/or freezers herein). These refrigerators and/or freezers may include integrated built in locking mechanisms that are electronically controllable to be in either a locked or unlocked stated. Other types of refrigerators and/or freezers may also be employed, including those with after-market installed locking mechanisms, either on the exterior or interior of the refrigerator/freezer. The storage unit may have a left or right handed door or entry point.

The locking mechanisms are capable of limiting access to the storage unit via electronic control. Some examples of non-environmentally controlled storage units include lock boxes, cabinets (both over and under counter), drawers, closets, and storage rooms. The entry points to these storage units may have locking mechanisms as described above. Any environmental control or monitoring system discussed herein is only applicable to environmentally controlled storage unit embodiments such as those having refrigerators and/or freezers.

The system may also include a control station communicatively coupled with the storage unit. The communication link may have any hardware and/or software necessary to facilitate communication between the control station and the storage unit. In some embodiments the control station may be capable of receiving any information provided and transmitted by the storage unit, and transmitting any instruction capable of being performed by the storage unit discussed herein. The control station may be located either locally or remote to the storage unit. Either wired or wireless communication methods may be used to establish the communication link. In some embodiments, the control station may be at least 50 feet from the storage unit.

In some embodiments the control station may control and monitor one or more of three primary functions: access control, environmental control (usually temperature, but possibly humidity, pressure, and/or other environmental parameters), and inventory control. In these embodiments, the storage unit will have any means necessary to acquire and transmit data relevant to such controls to the control station. Likewise, the control station will have any means necessary to receive such data and transmit instructions relevant to such controls to the storage unit.

In some embodiments, the control station may receive temperature information from the storage unit. The control station may determine whether or not the temperature is outside a predefined range. The control station may, in response to this determination control the storage unit's environmental control system, in the case of a refrigerator or freezer, the unit's refrigeration cycle, to maintain the temperature. If the temperature of the storage unit falls outside the predefined range, either above or below, the control station may cause an alarm to be generated. The alarm may include visual and/or audible indicators at the control station.

The control station may include a visual interface, such as a monitor or display screen, possibly with a touch screen or other input device such as a keyboard and mouse. The visual interface may provide an interaction point for the use to manipulate the control station, and by extension, the storage unit. For example, a user may be able to define the predefined temperature range. In some embodiments, for refrigerator/freezer storage units, this range may have a high and low point definable between −6° and 37° F.

Temperature readings may be received by the control station continuously, or at predefined intervals of time. Both the predefined intervals of time, and the temperature range which defines when an alarm will generate, may be defined by a user. The control station may cause the received temperature readings to be stored, either local to the control station, or remotely, possibly at a data storage system which stores information for a plurality of control stations, which in turn may each control/monitor a plurality of storage units. A user may be able to define identification (or naming) of any particular storage unit or control station, either at a control station or at the data storage system.

Again, while the control station may receive temperature readings continuously or at certain intervals, the control station may cause such readings to be stored at yet another interval (or possibly continuously). This interval may also be defined by a user at the control station. In some embodiments, the control station may only cause temperature information to be stored when the temperature of the storage unit is outside the predefined range (i.e., when the alarm is activated). One example interval of time may be every 30 minutes. In other embodiments, any time interval between one minute and 120 minutes may be employed.

In some embodiments, when an alarm is generated, indicators may be generated besides any visual and/or audible indicators generated at the control station. This may, for example, occur via a visual or audible indicator at the storage unit, or at the data storage system. Additionally, when an alarm is generated, a bulletin may be displayed or printed at the control station and/or data storage system.

The bulletin may be displayed or printed at predefined intervals until the temperature is back within the predefined range. Again, the intervals at which the bulletin is displayed or printed may be defined by the user at the control station or data storage system. The bulletin may include a plurality of fields including identification of the storage unit, a date and time, the temperature of the storage unit when the alarm was generated and/or when the bulletin was displayed/printed. The bulletin may also include a field which allows a user to input/write what was done to resolve the alarm condition, and to affirm, possibly via signature, their responsibility for handling the bulletin.

In yet other embodiments, the control station may be able to cause audible or visual alarms when the change of temperature over time exceeds a certain predefined amount. The type of alarm expressed by the control station or storage unit may differ from that expressed by the outside-of-temperature-range alarm.

As previously discussed, the above method implemented by the storage unit, control station, and/or data storage system may also be implemented to control/monitor other environmental parameters. These parameters may include, for example, humidity, pressure, etc. Any sensor for monitoring temperature or other parameters in the storage unit, as well as the locking mechanism of the storage unit, may be replaceable by the user. Any such sensor may be either shared with the storage unit's independent environmental monitor/control system, or independent thereto.

The control station may also be configured to receive user authentication information from a user, and upon verification of the user authentication information, send unlock instructions to the locking mechanism of the storage unit. The user authentication information may include a user name and a password, pin number, or other string. In some embodiments, a pin number may specify both the user and their authority to use the functions of the control station.

The storage unit may include a visual indicator which displays the current locked or unlocked state of the storage unit. Merely by way of example a light emitting diode may be either activated or inactivated when the unit is unlocked. This visual indicator may be tested by a user via instructing the control station to change the visual state of the visual indicator. In some embodiments, the lock mechanism itself may also be tested at the control station.

The control station may also be capable of receiving information from a sensor or sensors on the storage unit which reflect the current position of the door, or other entry point, of the storage unit. In some embodiments, the control station may cause an alarm to generate if it detects that the door or other entry point of the storage unit remains open beyond a user predefined length of time. Similarly, the control station may also be capable of monitoring and controlling any light sources inside the storage unit.

In some embodiments, the control station may receive information from a user identifying what medications and/or other items are stored within the storage unit. The control station may cause such information to be stored, along with a time stamp or other indicator which specifies when such stocking occurred. Thereafter, the control station may store temperature over time data related to each medication and/or other items stored within the storage unit.

A user may be able to specify another acceptable temperature range for each medication and/or other item stored within the storage unit. This acceptable temperature range may be different from that specified for the storage unit as a whole. In some embodiments, the acceptable temperature range for a particular medication and/or other item may be narrower than the predefined temperature range for the storage unit as a whole (i.e., the acceptable temperature range will be a subset or sub-range of the predefined temperature range for the storage unit).

Alarm data for alarms that occur while any particular medication and/or other item that is stored in the storage unit may also be stored for each such particular medication and/or other item. Therefore, whenever an alarm state occurs, information related to that alarm would be stored as particularly relating to medications and/or other items stored, such that a user or functions of the control station could reference such occurrences at a later date.

In some embodiments, a user may be able to specify to the control station that for any particular medication and/or item stored in the storage unit, access shall be limited or prohibited to such medication and/or item if an alarm has issued for the storage unit during the time the particular medication and/or item was stored in the storage unit. As an example, a user could specify that when a user enters authentication information into the control station and requests withdrawal of a certain medication and/or other item in a storage unit, a warning screen would be presented to the user indicating that at least one alarm condition has issued during the medication/item's storage in the storage unit. The user may be required to acknowledge receipt of such warning before access is allowed. In another embodiment, access to such medications/items which have experienced an alarm condition during their storage may be prohibited (and thus denial of deactivation of the locking mechanism on the storage unit). This may be a condition especially specified for medications/items where temperature control of the medications/items is critical to their viability.

Whatever the type of warning/prohibition, a user may specify which particular conditions cause what particular actions by the control station when withdrawal of an alarm affected medication/item is requested. For example, one or more limits on the amount of time a medication/item has spent outside of predefined ranges may be specified which in turn cause either a warning to be presented to a user requesting withdrawal, or access to be prohibited. In another example, one or more limits on the extent of temperature variance outside the predefined range may be specified which in turn cause either a warning to be presented to a user requesting withdrawal, or access to be prohibited. In yet another example, an algorithm which is a function of time spent by the medication/item outside of the predefined range, along with the temperature of the medication/item over such time may be specified which determines when a warning will be presented to a user requesting withdrawal, and/or access will be totally prohibited.

In some embodiments the control station and storage unit are configured such that if either the control station or the storage unit lose power, the locking mechanism of the storage unit will remain in a locked state. In other embodiments, the reverse will be true, and the storage unit will unlock under loss of power conditions. In any of the aforementioned embodiments, manual procedures may be available to open the storage unit. For example, the storage unit may have manual override unlocks, possibly that depend on the use of one, two, or more different keys/locks. In many embodiments, the control station and/or the storage until will have a battery or other backup power source in case of main power failure.

In some embodiments, at least a portion of the user authentication information received over time by the control station may be stored by the control station, or by the data storage system. The control stations and/or data storage system may also be able to conduct inventory control processes (either automatically via storage unit internal sensors, or via user input). This information may also be stored by the control system of data storage system.

In some embodiments, a user may be able to generate visually displayed or printed reports at either one or both of a control station or the data storage system. These reports may be available on-demand to a user, or may be set to be displayed/printed by the control station/data storage system at user predefined intervals. The type of information presented in any report may be predefined by a user, and may include any of the information discussed herein related to access control, inventory control, and/or environmental control. Note that any temperature data may be displayed/printed in either or both of degrees Celsius or degrees Fahrenheit.

In some embodiments, any failure of any one part of the invention, be it a portion or the entirety of the storage unit, the control system, and/or the data storage system, shall not cause failure of any other portion of the system. This may at least assist in ensuring security and viability of any items stored in the storage unit. For example, in many embodiments, failure of the locking mechanism of a storage unit will not cause failure of the temperature control/monitoring in that storage unit. Likewise, failure of the temperature control/monitoring functions will not cause failure of the locking mechanism.

Turning now to FIG. 1, a structure diagram of a system 100 of the invention for controlling and monitoring access and/or environmental parameters of medical storage units is shown. As discussed above, system 100 may include at least one control station 110 which is in communication with data storage system 120. Each control station 110 may be in communication with, and controlling/monitoring, various storage units 130.

Storage unit 130A may be a refrigerator with an integrated locking mechanism. Storage unit 130B may be a refrigerator with a retrofitted after-market locking mechanism. Storage unit 130C may be a freezer with an integrated locking mechanism. Storage unit 130D may be a closet, pantry or other secured room. Storage unit 130E may be above counter cabinets, and storage unit 130F may be below counter cabinets.

As described above, should any storage unit 130 for which environmental parameters are being monitored reach conditions which fall outside predefined ranges, control station 110 would cause an alarm to occur. Additionally, control station 110 may be able to monitor for unauthorized attempted access at each storage unit 130, and issue alarms and/or store records related to such unauthorized attempted access.

Each storage unit may include a visual indicator 140 as discussed above. In this embodiment, each visual indicator 140 indicates that its associated storage unit is locked. To unlock a particulate storage unit 130, a user would first input their authentication information at control station 110. Upon verification of the authentication information, the user would then be allowed to specify to control station 110 which storage unit they wish to access. Upon selection of the desired storage unit, control station 110 would cause storage unit 130 to unlock, and visual indicator 140 at that storage unit would change states to indicate the lock's unlocked status.

Figure 2:
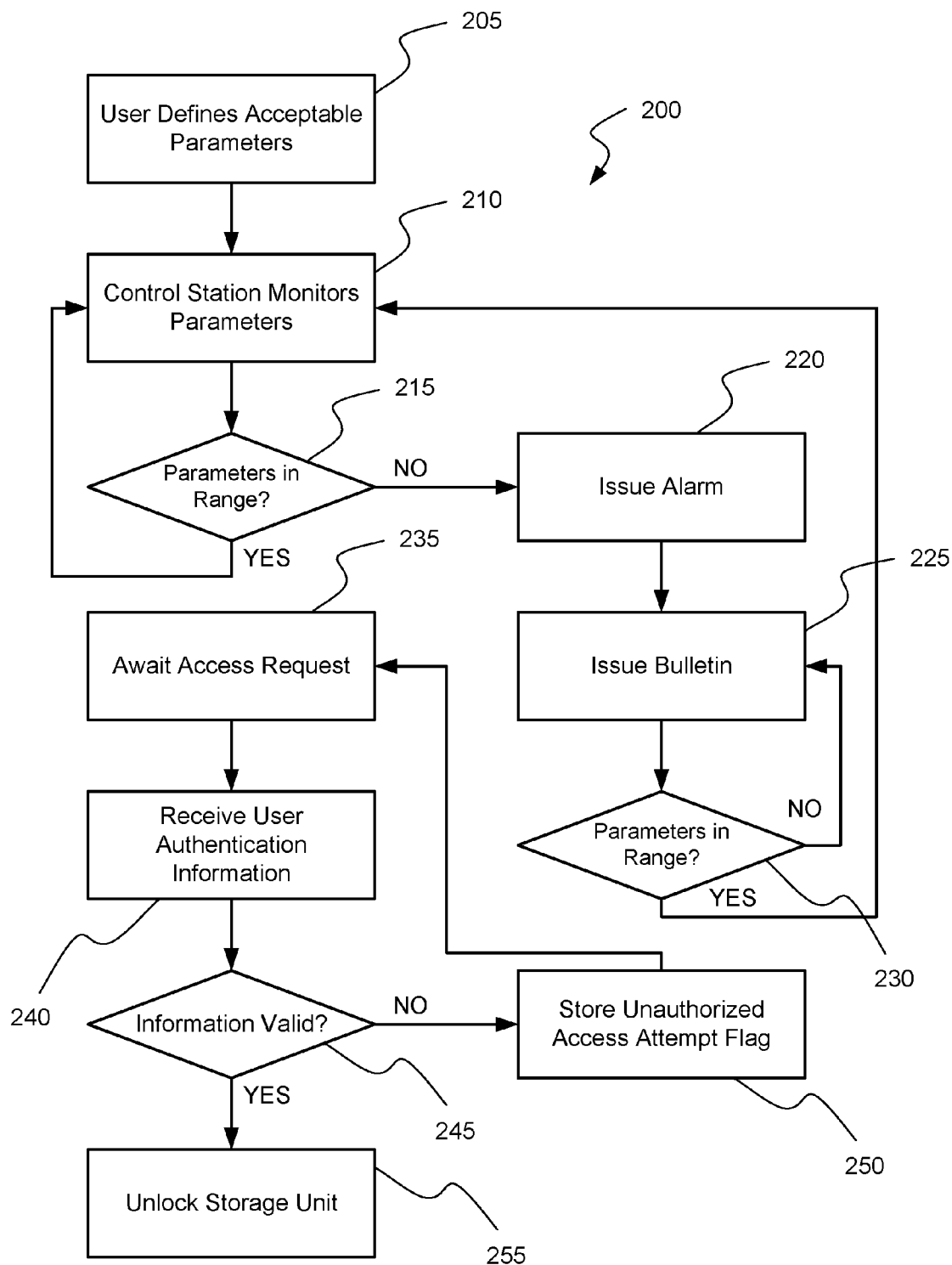
FIG. 2 is a flow diagram of a method of the invention for controlling and monitoring access and/or environmental parameters of medical storage units.

FIG. 2 shows a flow diagram of a method 200 of the invention for controlling and monitoring access and/or environmental parameters of medical storage units. At block 205, a user defines acceptable environmental parameters for a storage unit at a control station. At block 210, the storage unit monitors the environmental parameters of the storage unit. At block 215, if the environmental parameters fall outside the acceptable range, an alarm is issued at block 220.

At block 225, a bulletin is issued by the control station. At block 230, after a predefined interval of time, it is checked to see if the environmental parameter has returned to the acceptable range. If not, the bulletin is reissued at block 225. If the environmental parameter has returned to the acceptable range, the monitoring process continues at block 210.

Simultaneously, method 200 also includes at block 235 awaiting an access request by a user. At block 240 an access request with authentication information is received from a user at a control station. At block 245, it is determined if the authentication information is valid. If not, at block 250 an unauthorized access attempt flag is stored. If the authentication information is valid, then at block 255 access is granted and an unlock command is sent to the desired storage unit.

Figure 3:
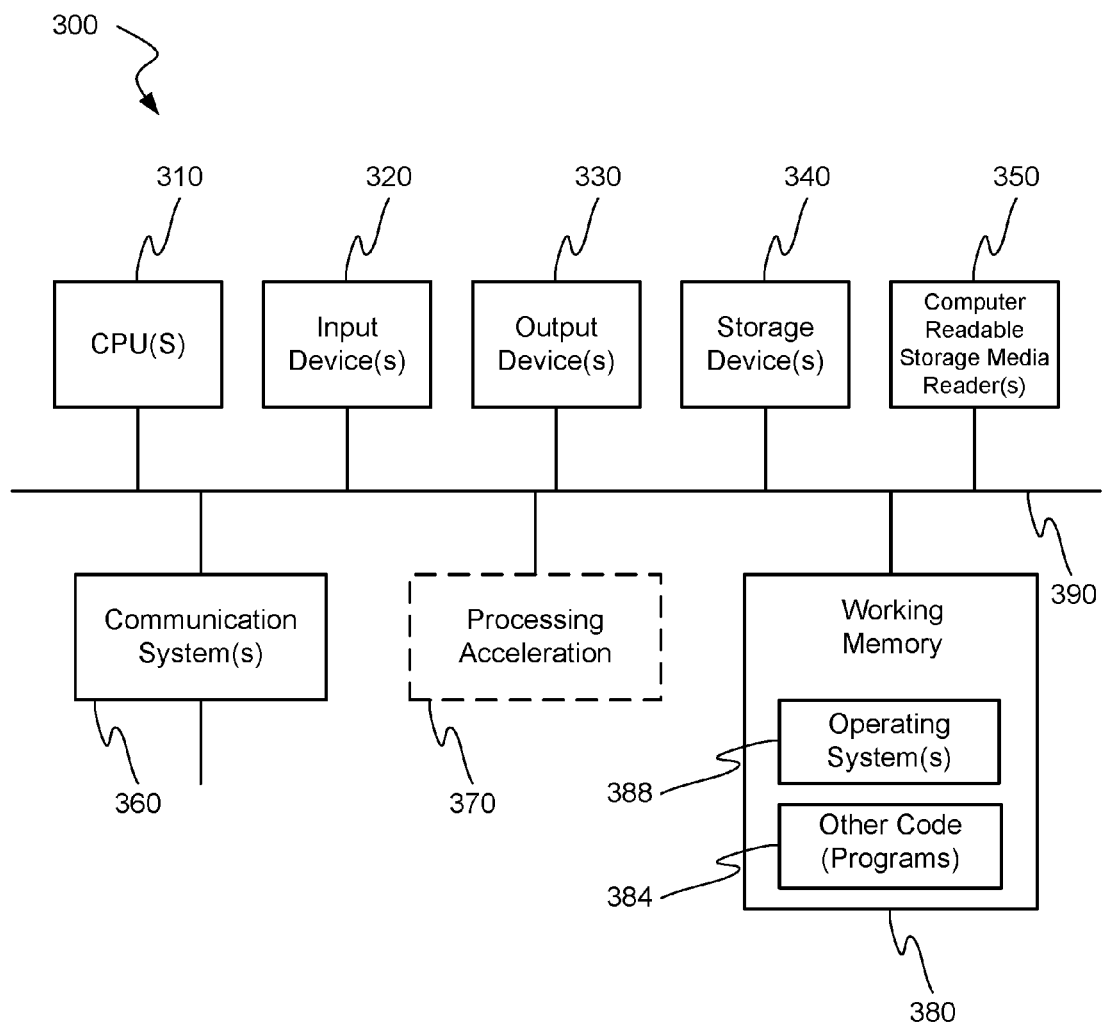
FIG. 3 is a block diagram of an exemplary computer system capable of being used in at least some portion of the apparatuses or systems of the present invention, or implementing at least some portion of the methods of the present invention.

FIG. 3 is a block diagram illustrating an exemplary computer system 300 in which embodiments of the present invention may be implemented. This example illustrates a computer system 300 such as may be used, in whole, in part, or with various modifications, to provide the functions of the control station, the central data system, the storage unit, and/or other components of the invention such as those discussed above. For example, various functions of the control station may be controlled by the computer system 300, including, merely by way of example, receiving information from the user, visually or audibly notifying the user, receiving information from the storage unit, controlling particular components of the storage unit, etc.

The computer system 300 is shown comprising hardware elements that may be electrically coupled via a bus 390. The hardware elements may include one or more central processing units 310, one or more input devices 320 (e.g., a mouse, a keyboard, etc.), and one or more output devices 330 (e.g., a display device, a printer, etc.). The computer system 300 may also include one or more storage device 340. By way of example, storage device(s) 340 may be disk drives, optical storage devices, solid-state storage device such as a random access memory ("RAM") and/or a read-only memory ("ROM"), which can be programmable, flash-updateable and/or the like.

The computer system 300 may additionally include a computer-readable storage media reader 350, a communications system 360 (e.g., a modem, a network card (wireless or wired), an infra-red communication device, Bluetooth™ device, cellular communication device, etc.), and working memory 380, which may include RAM and ROM devices as described above. In some embodiments, the computer system 300 may also include a processing acceleration unit 370, which can include a digital signal processor, a special-purpose processor and/or the like.

The computer-readable storage media reader 350 can further be connected to a computer-readable storage medium, together (and, optionally, in combination with storage device(s) 340) comprehensively representing remote, local, fixed, and/or removable storage devices plus storage media for temporarily and/or more permanently containing computer-readable information. The communications system 360 may permit data to be exchanged with a network, system, computer and/or other component described above.

The computer system 300 may also comprise software elements, shown as being currently located within a working memory 380, including an operating system 384 and/or other code 388. It should be appreciated that alternate embodiments of a computer system 300 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 300 may include code 388 for implementing any or all of the function of the various elements of the architecture as described herein. For example, software, stored on and/or executed by a computer system such as system 300, can provide the functions of the control station, the data storage system, the storage unit, and/or other components of the invention such as those discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A system comprising:
a control station, wherein the control station:
  receives temperature information from a refrigerated medical storage unit, wherein the temperature information includes a temperature of the refrigerated medical storage unit;
  receives information identifying a particular temperature range related to a particular item;
  receives information directing the control station to take a particular action in response to a withdrawal request for the particular item when the particular item has experienced storage outside the particular temperature range;
  causes at least a portion of the temperature information to be stored;
  determines whether the temperature is outside a predefined range; and
  causes a bulletin to be displayed or printed at predefined intervals when the temperature is outside the predefined range, until the temperature is back within the predefined range.

2. The system of claim 1, wherein the bulletin comprises:
an identification of the refrigerated medical storage unit;
a date and time;
a temperature; and
an acknowledgement or signature line or field for a user.

3. The system of claim 1, wherein the control station further:
  receives information identifying what items are stored in the refrigerated medical storage unit;
  receives information identifying what items are withdrawn from the refrigerated medical storage unit; and
  causes at least a portion of the temperature information to be stored indicating the temperature of each item in the refrigerated medical storage unit versus time.

4. The system of claim 1, wherein the particular action comprises:
  causing a warning to be presented to a user attempting to withdraw the particular item from the refrigerated medical storage unit; or
  causing access to the refrigerated medical storage unit to be prohibited.

5. The system of claim 4, wherein:
whether the warning is presented or access is prohibited is based at least in part on an algorithm which is a function of time spent by the particular item outside the particular temperature range and the temperature of the particular item during the time outside the particular range.

6. The system of claim 1, wherein:
the system further comprises the refrigerated medical storage unit, wherein the refrigerated medical storage unit comprises:
  a reversible locking mechanism to secure a door of the refrigerated medical storage unit while in a closed position; and
  a visual indicator which changes from a first state to a second state when the refrigerated medical storage unit is unlocked; and
the control station further:
  receives instructions from a user to test the visual indicator; and
  causes the visual indicator to change from the first state to the second state in response to the instructions to test the visual indicator.

7. A system comprising:
a control station, wherein the control station:
  receives temperature information from a refrigerated medical storage unit, wherein the temperature information includes a temperature of the refrigerated medical storage unit;
  receives information identifying a particular temperature range related to a particular item;
  receives information directing the control station to take a particular action in response to a withdrawal request for the particular item when the particular item has experienced storage outside the particular temperature range;
  causes at least a portion of the temperature information to be stored;
  determines whether the temperature is outside a predefined range; and
  causes a bulletin to be displayed or printed when the temperature is outside the predefined range, wherein the bulletin comprises:
    an identification of the refrigerated medical storage unit;
    a date and time;
    a temperature; and
    an acknowledgement or signature line or field for a user.

8. The system of claim 7, wherein:
the bulletin is printed or displayed at predefined intervals until the temperature is back within the predefined range.

9. The system of claim 7, wherein the control station further:
  receives information identifying what items are stored in the refrigerated medical storage unit;
  receives information identifying what items are withdrawn from the refrigerated medical storage unit; and
  causes at least a portion of the temperature information to be stored indicating the temperature of each item in the refrigerated medical storage unit versus time.

10. The system of claim 7, wherein the particular action comprises:
  causing a warning to be presented to a user attempting to withdraw the particular item from the refrigerated medical storage unit; or
  causing access to the refrigerated medical storage unit to be prohibited.

11. The system of claim 10, wherein:
whether Previously Presented warning is presented or access is prohibited is based at least in part on an algorithm which is a function of time spent by the particular item outside the particular temperature range and the temperature of the particular item during the time outside the particular range.

12. The system of claim 7, wherein:
the system further comprises the refrigerated medical storage unit, wherein the refrigerated medical storage unit comprises:
- a reversible locking mechanism to secure a door of the refrigerated medical storage unit while in a closed position; and
- a visual indicator which changes from a first state to a second state when the refrigerated medical storage unit is unlocked; and the control station further:
- receives instructions from the user to test the visual indicator; and
causes the visual indicator to change from the first state to the second state in response to the instructions to test the visual indicator.

13. A system comprising:
a control station, wherein the control station:
- receives temperature information from a refrigerated medical storage unit, wherein the temperature information comprises temperature versus time information;
- receives information identifying a particular temperature range related to a particular item;
- receives information directing the control station to take a particular action in response to a withdrawal request for the particular item when the particular item has experienced storage outside the particular temperature range;
- determines whether the temperature is outside a predefined range;
- causes temperature versus time information to be stored only when the temperature is outside the predefined range; and
- causes an alarm to be generated when the temperature is outside the predefined range.

14. The system of claim 13, wherein the control station further:
causes a bulletin to be displayed or printed at predefined intervals when the alarm is generated, until the temperature is back within the predefined range.

15. The system of claim 13, wherein the control station further:
- receives information identifying what items are stored in the refrigerated medical storage unit;
- receives information identifying what items are withdrawn from the refrigerated medical storage unit; and
- causes at least a portion of the temperature information to be stored indicating the temperature of each item in the refrigerated medical storage unit versus time.

16. The system of claim 13, wherein the particular action comprises:
- causing a warning to be presented to a user attempting to withdraw the particular item from the refrigerated medical storage unit; or
- causing access to the refrigerated medical storage unit to be prohibited.

17. The system of claim 16, wherein:
whether the warning is presented or access is prohibited is based at least in part on an algorithm which is a function of time spent by the particular item outside the particular temperature range and the temperature of the particular item during the time outside the particular range.

* * * * *